(12) United States Patent
Zhu et al.

(10) Patent No.: US 9,404,819 B2
(45) Date of Patent: Aug. 2, 2016

(54) UNIVERSAL MOUNT BICYCLE POWER METER MODULE

(71) Applicants: Shengbo Zhu, San Jose, CA (US); Su Shiong Huang, Bellevue, WA (US)

(72) Inventors: Shengbo Zhu, San Jose, CA (US); Su Shiong Huang, Bellevue, WA (US)

(73) Assignee: SILICON VALLEY MICRO E CORPORATION, San Jose, CA (US)

( * ) Notice: Subject to any disclaimer, the term of this patent is extended or adjusted under 35 U.S.C. 154(b) by 261 days.

(21) Appl. No.: 14/120,912

(22) Filed: Jul. 9, 2014

(65) Prior Publication Data

US 2016/0008663 A1 Jan. 14, 2016

(51) Int. Cl.
*G01L 3/00* (2006.01)
*G01L 3/10* (2006.01)
*A61B 5/22* (2006.01)

(52) U.S. Cl.
CPC .................. *G01L 3/108* (2013.01); *A61B 5/224* (2013.01); *B62K 2207/00* (2013.01)

(58) Field of Classification Search
CPC ....... G01L 1/2256; G01L 1/22; G01L 5/0095; B62J 2099/002; B62K 2207/00; A61B 5/1118; A61B 5/6895

USPC .................................. 702/33, 41, 44; 482/8
See application file for complete search history.

(56) References Cited

U.S. PATENT DOCUMENTS

| | | | |
|---|---|---|---|
| 7,792,648 B2 * | 9/2010 | Kalliomaki | A61B 5/221 702/44 |
| 8,336,400 B2 * | 12/2012 | Lassanske | B60B 27/0068 73/862.29 |
| 9,063,026 B2 * | 6/2015 | Nassef | B60L 11/007 |

* cited by examiner

*Primary Examiner* — An Do

(57) ABSTRACT

A universal mount bicycle power meter module has a base member with first and second ends and a narrow central portion which is relatively compressible in response to applied forces. Firmly secured to the first end is an internally threaded mounting nut in registration with an aperture in the first end. The nut secures the first end of the base member to an externally threaded end portion of a bicycle axle. The second end of the base member is configured to be firmly secured to a rear frame portion of a bicycle using a mounting clamp. A strain gauge sensor assembly is mounted on the central portion of the base member to generate resistance values representative of the amount of compression in the central portion. The sensor assembly is coupled to a signal processing unit having circuitry for converting the resistance values and bicycle velocity signals from an associated bicycle speedometer to cyclist power signals.

14 Claims, 8 Drawing Sheets

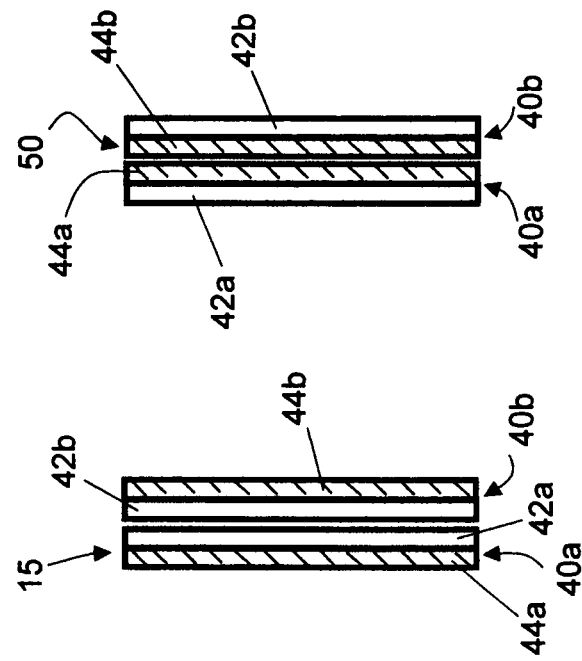
FIG. 9
FIG. 8
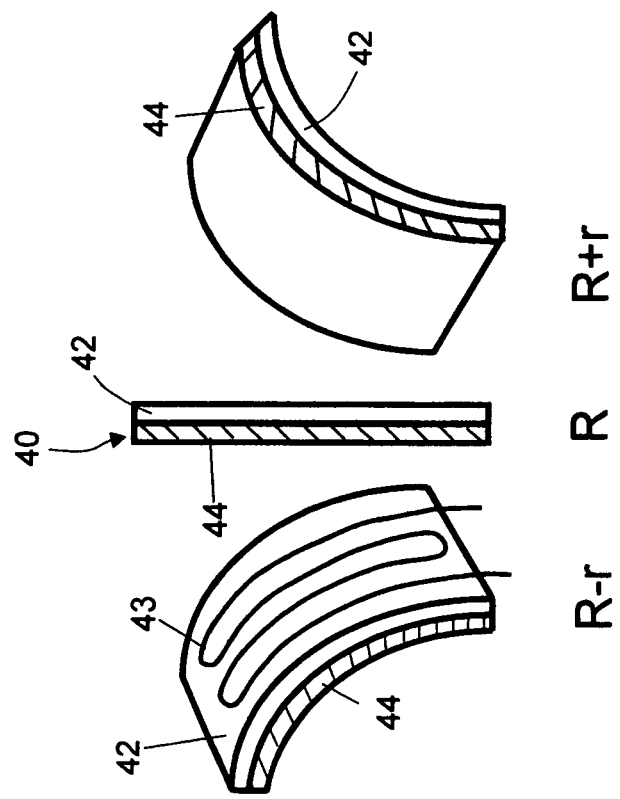
FIG. 7

UNIVERSAL MOUNT BICYCLE POWER METER MODULE

BACKGROUND OF THE INVENTION

This invention relates to bicycle power meters used to indicate the amount of power expended by the bicyclist during cycling. More particularly, this invention relates to a universal mount bicycle power meter module capable of being fitted to any bicycle for enabling the generation of electrical signals from which power can be determined.

Bicycle power meters are being increasingly used by both professional and amateur cyclists as an aid in developmental training. Several different types of bicycle power meters are available, some of which use strain gauges to measure the force applied by the cyclist to the crankset, the bottom bracket or the rear wheel hub. While effective in providing electrical signals representative of applied force, known bicycle power meters using strain gauges are relatively expensive and somewhat difficult to install.

Commonly assigned U.S. Pat. No. 8,370,087 issued Feb. 5, 2013 for "Bicycle Power Meter With Frame Mounted Sensor" discloses a bicycle power meter which is relatively inexpensive and easy to install at the point of manufacture, at the retail level and by the end user. The bicycle power meter has a strain gauge sensor assembly mounted on a relatively compressible web portion of the end of the rear fork of the bicycle frame. The relatively compressible web portion is near the rear hub and subject to the forces exerted by the cyclist to the crankset, and transferred via the chain, and sprocket assembly to the hub. The sensor assembly has two ohmically interconnected stretch sensors each having a first layer bearing a variable resistance element, whose resistance changes with displacement of the compressible web portion, and a second layer for providing support for the first layer. The sensor assembly is connected in a bridge circuit to two other resistances to generate signals representative of cyclist applied force. These signals are processed along with velocity signals to generate power signals and the power signals are supplied to a display. While this bicycle power meter overcomes the disadvantages inherent in previously known bicycle power meters, the application is limited to those bicycles having the relatively compressible web portion of the bicycle frame. Not all bicycle frames have this construction.

SUMMARY OF THE INVENTION

The invention comprises a universal mount bicycle power meter module which can be mounted to any bicycle having a rear axle with an externally threaded end portion and a rear frame portion. The universal mount bicycle power meter is relatively inexpensive but effective in providing electrical signals representative of applied cyclist force, which signals can be combined with speed signals to generate real time power measurements.

In a first aspect the invention comprises a bicycle power meter module including an elongate base member having a first end with an aperture, a second end adapted to be secured to a bicycle frame portion adjacent a rear bicycle axle, and a compressible central portion; a strain gauge sensor assembly mounted on the compressible central portion, the strain gauge sensor assembly having first and second stretch sensors each including a first layer having a variable resistance element mounted thereon and a second layer for supporting the first layer, the variable resistance elements of the first and second stretch sensors being ohmically interconnected to present a total resistance value representative of cyclist force; a mounting nut firmly secured to the first end of the base member, the nut having a centrally located internally threaded through-hole in registration with the aperture in the first end of the base member so that the nut can be threaded onto an associated externally threaded bicycle axle end portion to secure the base member to the bicycle axle at the first end; and a signal processing unit mounted on the base member and electrically coupled to the strain gauge sensor assembly for converting the total resistance value to cyclist power signals.

The compressible central portion of the base member preferably has a width less that the width of the first and second ends of the base member to promote compression of the central portion under applied force.

The second end of the base member is preferably secured to the bicycle frame member using a mounting clamp secured to the second end of the base member, the mounting clamp having a mounting band adapted to firmly capture the bicycle frame portion.

The first and second stretch sensors may be arranged with each of the first layers in facing relation or with each of the second layers in facing relation.

The signal processing unit preferably includes a bridge circuit having the first and second stretch sensors connected in a first branch and a pair of fixed resistances connected in a second branch; an amplifier coupled to the bridge circuit for amplifying signals representative of the total resistance value; an analog-to-digital converter coupled to the amplifier for converting the signals output from the amplifier to digital signals; and a microcomputer coupled to the analog-to-digital converter for receiving the digital signals and bicycle velocity signals from an associated bicycle speedometer and converting the received signals to the power signals. In a preferred wireless embodiment, the signal processing unit further includes a transmitter coupled to the microcomputer for receiving the power signals and generating equivalent wireless signals; and a antenna coupled to the transmitter for broadcasting the equivalent wireless signals to an associated receiver.

In a second aspect the invention comprises the combination of a bicycle having a frame with a rear portion and a rear axle with an externally threaded end portion adjacent said rear portion of said frame; and a bicycle power meter module comprising an elongate base member having a first end with an aperture, a second end secured to the rear portion of the frame, and a compressible central portion; a strain gauge sensor assembly mounted on the compressible central portion, the strain gauge sensor assembly having first and second stretch sensors each including a first layer having a variable resistance element mounted thereon and a second layer for supporting the first layer, the variable resistance elements of the first and second stretch sensors being ohmically interconnected to present a total resistance value representative of cyclist force; a mounting nut firmly secured to the first end of the base member, the nut having a centrally located internally threaded through-hole in registration with the aperture, the nut being threaded onto the externally threaded axle end portion so that the base member is secured to the axle end portion at the first end of the base member; and a signal processing unit mounted on the base member and electrically coupled to the strain gauge sensor assembly for converting the total resistance value to cyclist power signals.

The compressible central portion of the base member preferably has a width less that the width of the first and second ends of the base member to promote compression of the central portion under applied force.

The second end of the base member is preferably secured to the bicycle frame member using a mounting clamp secured to the second end of the base member, the mounting clamp having a mounting band adapted to firmly capture the bicycle frame portion.

The first and second stretch sensors may be arranged with each of the first layers in facing relation or with each of the second layers in facing relation.

The signal processing unit preferably includes a bridge circuit having the first and second stretch sensors connected in a first branch and a pair of fixed resistances connected in a second branch; an amplifier coupled to the bridge circuit for amplifying signals representative of the total resistance value; an analog-to-digital converter coupled to the amplifier for converting the signals output from the amplifier to digital signals; and a microcomputer coupled to the analog-to-digital converter for receiving the digital signals and bicycle velocity signals from an associated bicycle speedometer and converting the received signals to the power signals. In a preferred wireless embodiment, the signal processing unit further includes a transmitter coupled to the microcomputer for receiving the power signals and generating equivalent wireless signals; and an antenna coupled to the transmitter for broadcasting the equivalent wireless signals to an associated receiver.

The invention greatly facilitates the inclusion of a bicycle power meter with any bicycle having a rear axle with an externally threaded end portion and a rear frame portion. The bicycle power meter module can be easily secured to the bicycle components at the point of manufacture. Similarly, the bicycle power meter module can be readily secured to the bicycle at any point in the distribution chain, such as at the retailer as an add-on option. The bicyclist can also add the bicycle power meter module to a bicycle after purchase, at relatively low cost and effort.

For a fuller understanding of the nature and advantages of the invention, reference should be made to the ensuing detailed description taken in conjunction with the accompanying drawings.

BRIEF DESCRIPTION OF THE DRAWINGS

FIG. 7 is a schematic view of a single strain gauge sensor illustrating the sensor in three different positions;

FIG. 8 is a schematic view of a first embodiment of a dual element strain gauge sensor assembly;

FIG. 9 is a schematic view of a second embodiment of a dual element strain gauge sensor assembly.

DETAILED DESCRIPTION OF THE PREFERRED EMBODIMENTS

Figure 1:
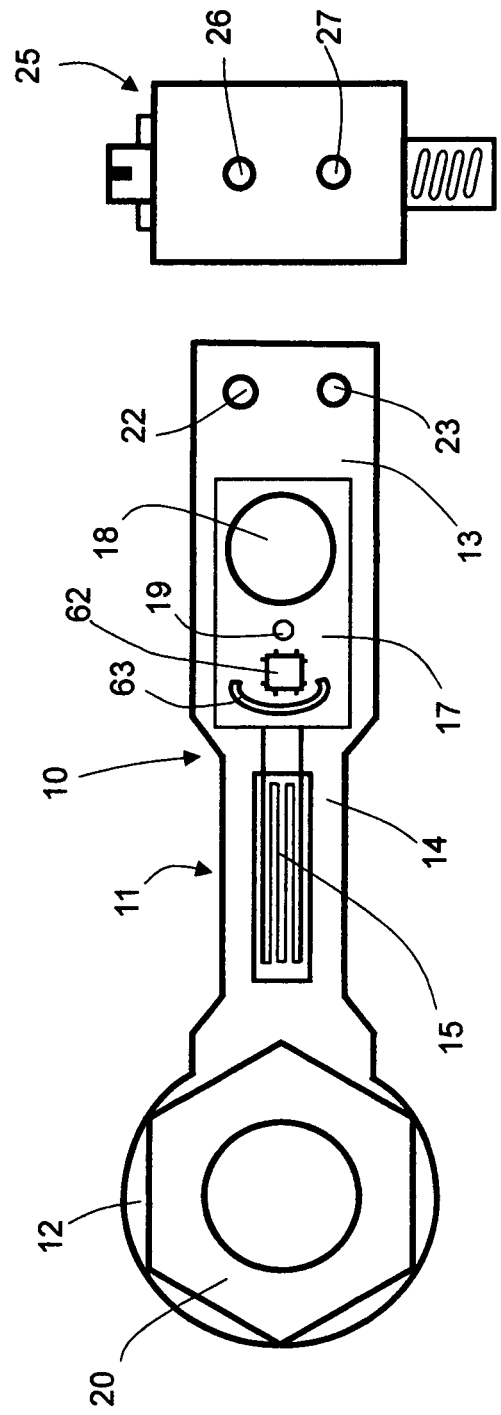
FIG. 1 is a plan view of a preferred embodiment of a bicycle power meter module incorporating the invention.

Turning now to the drawings, FIG. 1 is plan view of a first embodiment of a bicycle power meter module incorporating the invention. As seen in this Figure, a bicycle power meter module assembly generally designated with reference numeral 10 includes an elongate base member 11 having a first end portion 12, a second, opposite end portion 13, and a central portion 14 preferably with a narrower width than end portions 12, 13. Elongate base member 11 is fabricated from a relatively compressible, thin material, such as stainless steel having a thickness of 1.0 mm., in order to contract or expand in length in response to force applied to end 12.

Secured to the upper surface of central portion 14 is a strain gauge assembly 15 described more fully below with reference to FIGS. 7-9. Strain gauge assembly 15 has a pair of ohmic conductors which are electrically connected to the input terminals of a signal processing unit described more fully below with reference to FIG. 5 (wired version) and FIG. 6 (wireless version) mounted on a circuit board 17, which in turn is bonded to the upper surface of end portion 13 of base member 11. The signal processing unit is powered by a small battery 18 removably secured to circuit board 17 (as illustrated) or directly to the upper surface of end portion 13 of base member 11. Power from battery 18 to the signal processing unit is controlled by a manually operable on/off switch 19.

Secured to the upper surface of first end portion 12 of base member 11 is an internally threaded nut 20, which is used to secure bicycle power meter module 10 to one end of the rear axle of a bicycle. Nut 20 can be secured using a variety of techniques, such as welding, brazing, or gluing with a strong adhesive. What is important to the process of securing is nut 20 must be firmly secured to base member 11 so that relative motion between nut 20 and base member 11 is prevented. Stated differently, when the end of the bicycle axle to which nut 20 is threadably attached is deflected due to force applied by the bicycle chain, this deflection must be transferred to base member 11 via nut 20 so that strain gauge assembly 15 senses the amount of deflection.

Figure 4:
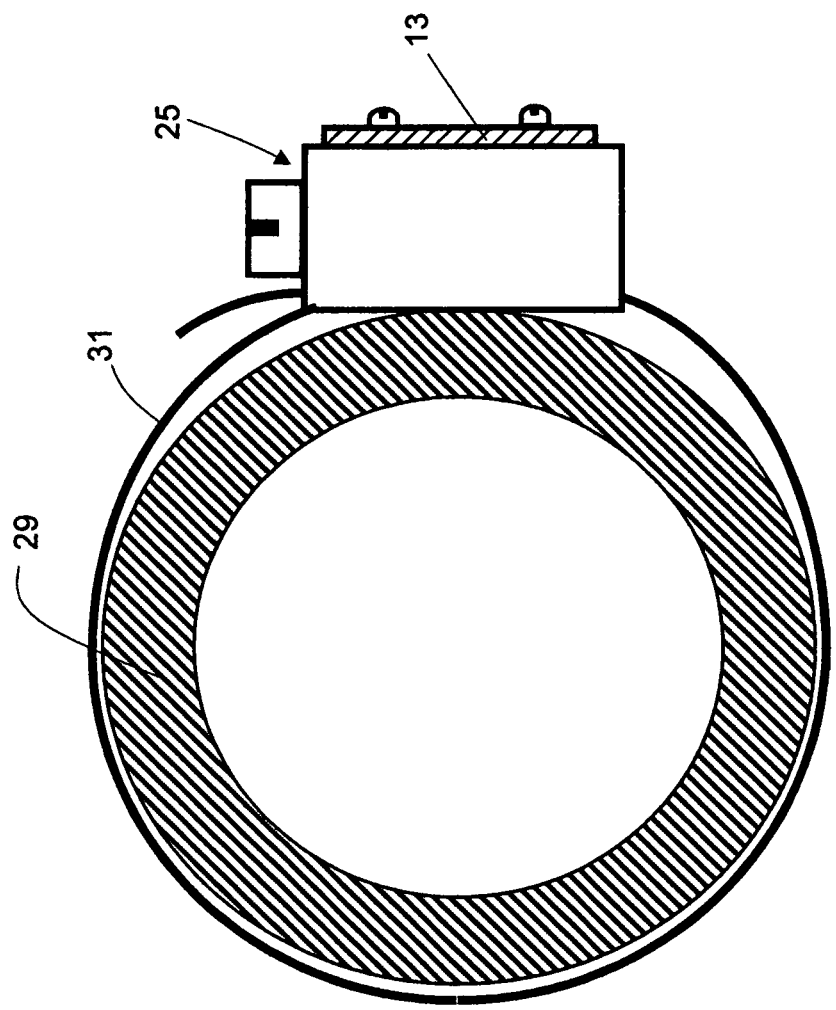
FIG. 4 is an enlarged sectional view taken along lines 4-4 of FIG. 2 illustrating the mounting clamp assembled to the bicycle frame.

The second, opposite end 13 of base member 11 is provided with a pair of mounting apertures 22, 23. A mounting clamp generally designated with reference numeral 25, preferably a conventional automotive hose clamp, is provided with a mating pair of mounting apertures 26, 27 so that end portion 13 can be secured to mounting clamp 25 in the manner depicted in FIGS. 2 and 4.

Figure 2:
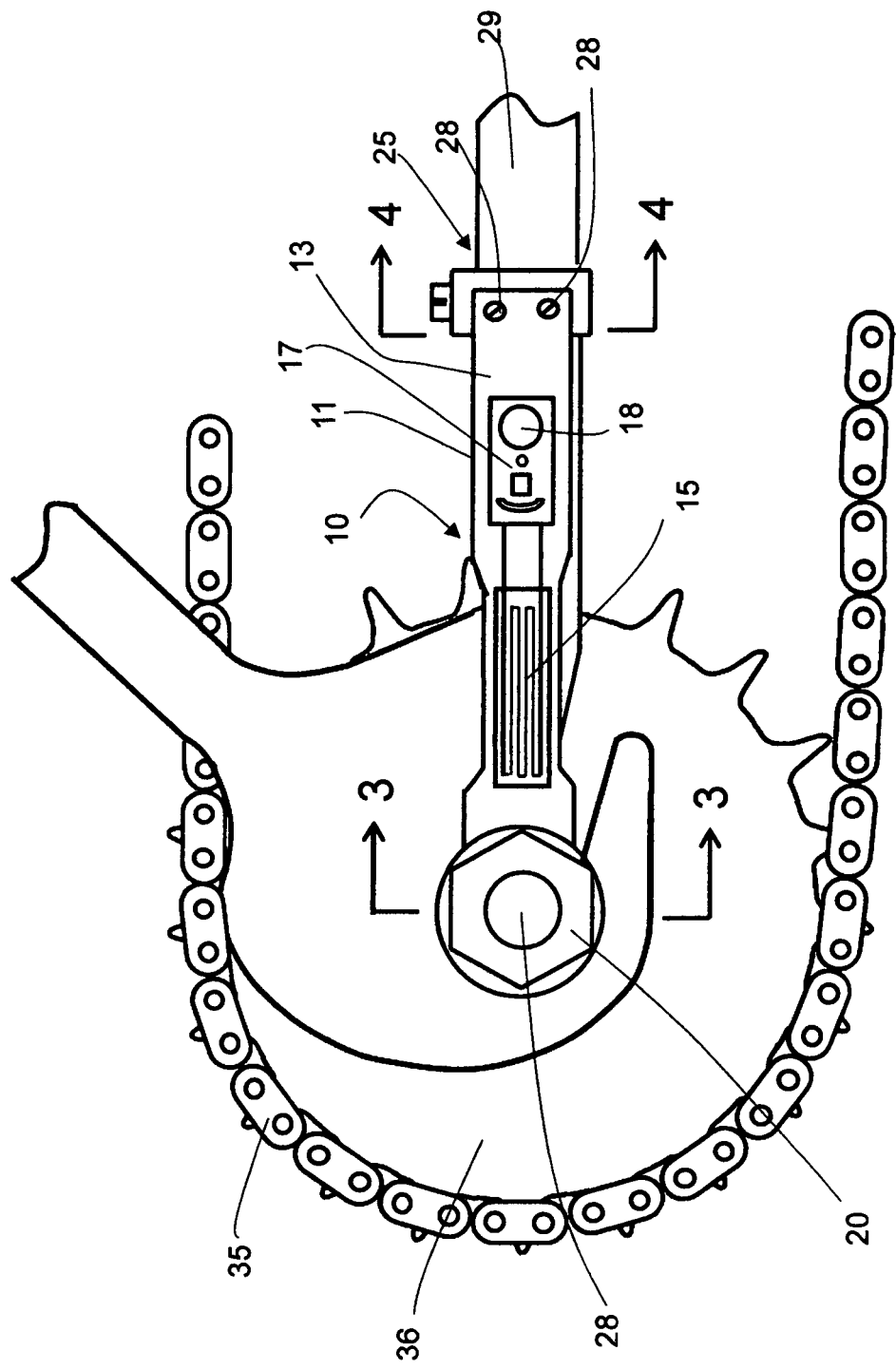
FIG. 2 is a partial plan view taken from the rear sprocket side of a bicycle illustrating the bicycle power meter module of FIG. 1 mounted in place.
Figure 3:
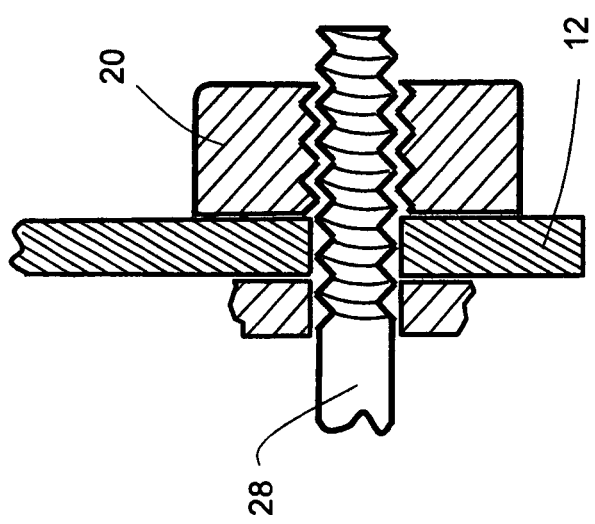
FIG. 3 is an enlarged sectional view taken along lines 3-3 of FIG. 2 illustrating the mounting nut, frame and module base assembly.

FIG. 2 is a partial plan view taken from the rear sprocket side of a bicycle illustrating the bicycle power meter module 10 of FIG. 1 mounted in place. With reference to this Figure, and FIGS. 3 and 4, mounting clamp 25 is first secured to opposite end 13 of the base member 11 using threaded fasteners 28 passing through apertures 22, 23, 26, 27. Next, module 10 is attached to the sprocket end of a threaded axle 28 by threading nut 20 onto the end of axle 28 until the base member 11 is firmly fixed in place with opposite end portion 13 aligned with portion 29 of the bicycle frame in the manner shown in FIG. 2. Next, opposite end 13 of base member is secured to portion 29 of the bicycle frame by passing the mounting band 31 of mounting clamp 25 around frame portion 29 and tightening the band 31 against the periphery of frame portion 29 until opposite end portion 13 is firmly secured to frame portion 29. This completes the mechanical mounting of bicycle power meter module 10.

In use, as a bicyclist applies force to the pedals attached to the crankset, drive chain 35 (FIG. 2) experiences a force which is transferred via sprocket 36 to axle 28, causing axle 28 to deflect in the horizontal direction. This deflection of axle 28 is transferred via base member 11 to strain gauge assembly 15, causing a change in the signal output from strain gauge assembly 15. The output signal is processed in the manner described below to generate power magnitude signals which can be displayed to the bicyclist.

FIG. 7 illustrates a simple stretch sensor 40 having the property of an ohmic resistance which varies in a predictable amount with linear longitudinal displacement of the sensor body. Stretch sensor 40 has a first layer 42 on which a thin variable resistance element 43 is mounted, and a second base layer 44 which carries the first layer and provides additional mechanical strength for sensor 40. The resistance value of sensor 40 depends upon the longitudinal displacement of the sensor body. As shown in FIG. 7, when sensor 40 is displaced in one direction (illustrated as flexing) in a first direction, the value of the resistance increases (R+r), where R is the at rest resistance value of sensor 40 and r is the additional resistance value due to the displacement in the first direction. Similarly, when sensor 40 is displaced in the opposite direction, the value of the resistance decreases (R−r).

FIG. 8 illustrates a strain gauge sensor assembly 15 of the type incorporated into the power meter configuration shown in FIGS. 1 and 2. As seen in this Figure, sensor assembly 15 comprises two two layer stretch sensors 40a, 40b having first layers 42a, 42b, and second layers 44a, 44b. Stretch sensors 40a, 40b are arranged with the first layers 42a, 42b in facing relation in an (R+r), (R−r) relation. As sensor assembly 15 is displaced by forces applied to axle 28 of right rear fork 12, the total resistance of each stretch sensor will vary in equal and opposite directions.

FIG. 9 illustrates an alternate strain gauge sensor assembly 50 of the type incorporated into the power meter configuration shown in FIGS. 1 and 2. As seen in this Figure, sensor assembly 50 comprises two two layer stretch sensors 40a, 40b having first layers 42a, 42b, and second layers 44a, 44b. Stretch sensors 40a, 40b are arranged with the second layers 44a, 44b in facing relation in an (R−r), (R+r) relation. As sensor assembly 50 is displaced by forces applied to axle 28 of right rear fork 12, the total resistance of each stretch sensor will vary in equal and opposite directions.

Figure 5:
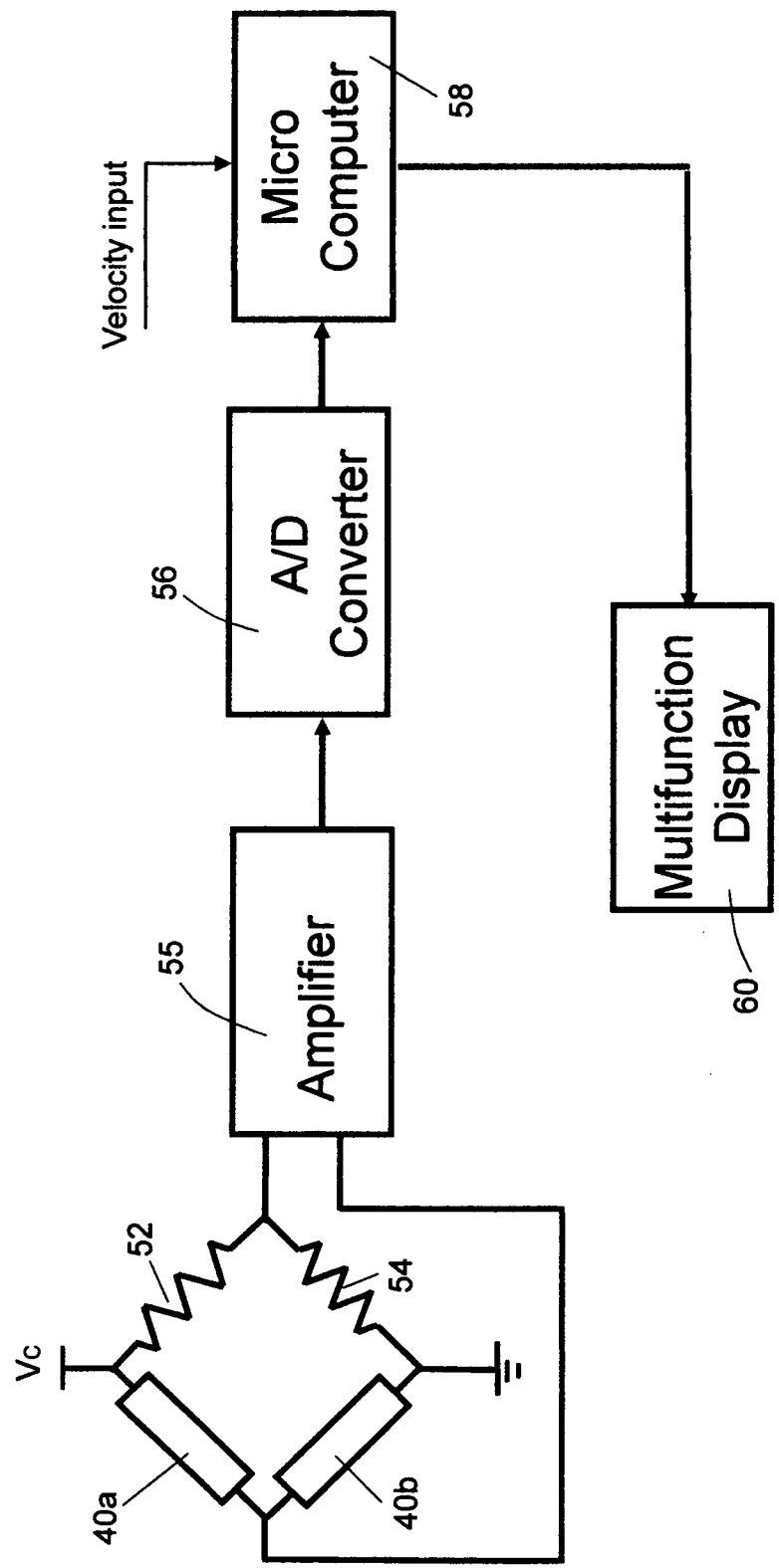
FIG. 5 is a block diagram of a bicycle power meter module using a single strain gauge sensor assembly configured as a wired unit.

FIG. 5 is a block diagram of a bicycle power meter unit using a single strain gauge sensor assembly configured as a wired unit. As seen in this Figure, the stretch sensors 40a, 40b comprising strain gauge sensor assembly 15 or 50 are connected to a pair of fixed resistances 52, 54 in a well-known Wheatstone bridge circuit configuration. The top node of the bridge is connected to a source of electrical potential Vc supplied by battery 18. The bottom node of the bridge is connected to circuit ground. The right node is connected to one end of the fixed resistances 52, 54 and serves as one output terminal of the bridge circuit. The second end of fixed resistance 52 is connected to one end of stretch sensor 40a and to supply voltage Vc. The second end of fixed resistance 54 is connected to one end of stretch sensor 40b and to circuit ground. The other ends of stretch sensors 40a, 40b are connected together and serve as the other output terminal of the bridge circuit.

The bridge circuit output terminals are coupled to the input terminals of an amplifier 55, where the bridge signals are amplified. Amplifier 55 is preferably a type MAX4197 unit available from MAXIM Corporation. The amplified signals output from amplifier 55 are coupled to the input of an analog-to-digital converter 56 which converts the amplified analog signals to digital equivalent signals. The digital signals output from analog-to-digital converter 56 are coupled to an input port of a microcomputer 58. Analog-to-digital converter 56 and microcomputer 58 are preferably combined in a type PIC 10F202 unit available from Microchip Corporation. Velocity signals from a bicycle speedometer (not shown) are also coupled to microcomputer 58. Microcomputer 58 processes the force signals and the velocity signals using a known algorithm to provide power magnitude signals. The power magnitude signals are coupled to a multifunction display 60, which displays the current power value in readable form by the bicyclist. In the FIG. 5 embodiment the units are coupled together by ohmic wire connections.

Figure 6:
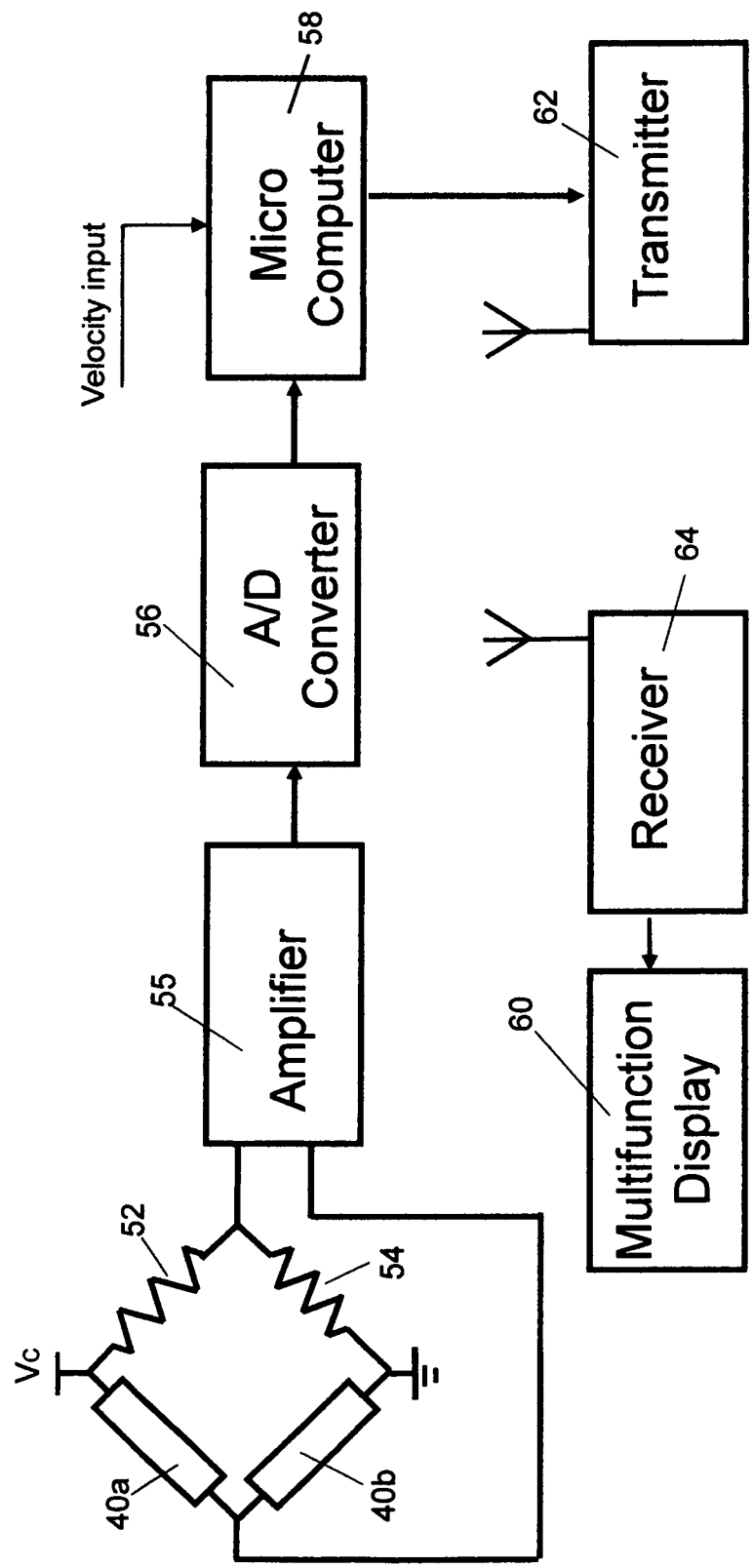
FIG. 6 is a block diagram of a bicycle power meter module using a single strain gauge sensor assembly configured as a wireless unit.

FIG. 6 is a block diagram of a bicycle power meter unit using a single strain gauge sensor assembly configured as a wireless unit. In this Figure, elements corresponding to the same elements in the system of FIG. 5 are designated with the same reference numerals. In the FIG. 6 system, the processed power signals are coupled to the input of an r.f transmitter 62 located on circuit board 17. Transmitter 62 is preferably a type nRF24AP2 ANT+ module available from Nordic Semiconductor Co. of Norway. Transmitter 62 transmits the power signals via an antenna 63 (FIG. 1) to a receiver 64 located near the multifunction display 60, which supplies these signals to the multifunction display 60.

In both the wired and wireless versions of the bicycle power meter unit, the strain gauge assembly 15, 50, amplifier 55, A/D converter 56, microcomputer 58, and transmitter 62 are all mounted on circuit board 17; while display 60 and receiver 64 are mounted in a convenient location for the cyclist to view the display, typically somewhere on the handle bars of the bicycle.

Figure 10:
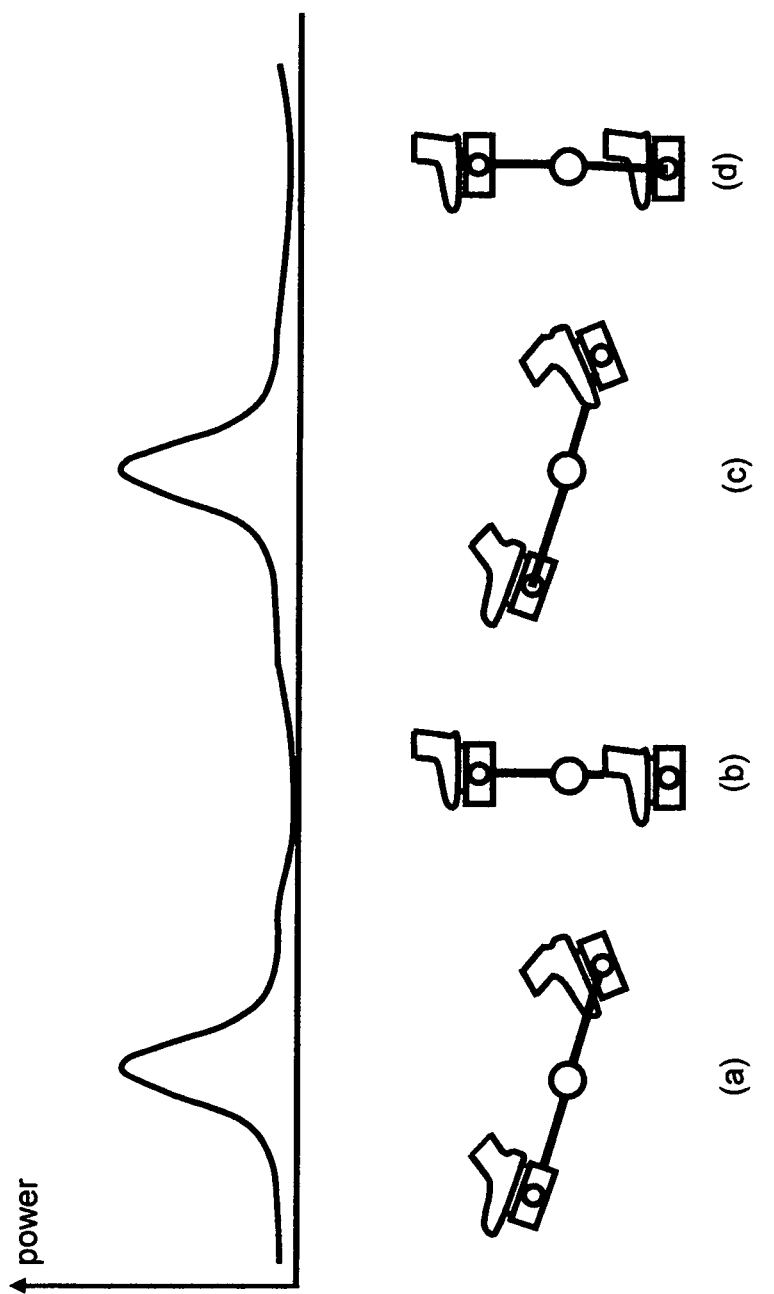
FIG. 10 is a schematic diagram illustrating variation in cyclist power with crankset angular position.

In use, as the cyclist applies force to the bicycle pedals, the magnitude of the force is monitored by the bridge circuit and converted to visible power display signals for the bicyclist to observe. FIG. 10 is a schematic diagram illustrating variation in cyclist power with crankset angular position. In position (a) the pedals are essentially horizontal and the cyclist is applying maximum force with the forward pedal. In position (b) the pedals are essentially vertical and the cyclist is applying minimum force. In position (c) the pedals are again essentially horizontal and the cyclist is applying maximum force with the forward pedal; while in position (d) the pedals are again essentially vertical and the cyclist is applying minimum force.

As will now be apparent, bicycle power meter modules fabricated according to the teachings of the invention offer cost and ease of installation advantages over known bicycle power meters using strain gauges. More particularly, the bicycle power meter module 10 is relatively simple to install on any bicycle having a threaded rear axle end portion onto which the nut 20 can be threaded and a rear frame portion around which the mounting band 31 of mounting clamp 25 can be secured. This installation can be done at the bicycle factory or elsewhere in the chain of commerce (e.g., by the retailer or the user-bicyclist). In addition, bicycle power meter modules fabricated according to the teachings of the invention can be configured in either a wired or a wireless mode, which affords great flexibility in the installation process.

While the invention has been described with reference to particular embodiments, various modifications, alternate constructions and equivalents may be employed without departing from the spirit of the invention. For example, while certain circuit components have been disclosed, other equivalent units may be employed, as desired. Therefore, the above should not be construed as limiting the invention, which is defined by the appended claims.

What is claimed is:

1. A bicycle power meter module comprising:
an elongate base member having a first end with an aperture, a second end adapted to be secured to a bicycle frame portion adjacent a rear bicycle axle, and a compressible central portion;
a strain gauge sensor assembly mounted on said compressible central portion, said strain gauge sensor assembly having first and second stretch sensors each including a first layer having a variable resistance element mounted thereon and a second layer for supporting said first layer, the variable resistance elements of said first and second stretch sensors being ohmically interconnected to present a total resistance value representative of cyclist force;
a mounting nut firmly secured to said first end of said base member, said nut having a centrally located internally threaded through-hole in registration with said aperture so that said nut can be threaded onto an associated externally threaded bicycle axle to secure said base member to the bicycle axle at said first end; and
a signal processing unit mounted on said base member and electrically coupled to said strain gauge sensor assembly for converting said total resistance value and bicycle velocity signals from an associated bicycle speedometer to cyclist power signals.

2. The bicycle power meter module of claim 1 wherein said compressible central portion of said base member has a width less that the width of said first and second ends to promote compression of said central portion under applied force.

3. The bicycle power meter module of claim 1 further including a mounting clamp secured to said second end of said base member, said mounting clamp having a mounting band adapted to firmly capture the bicycle frame portion.

4. The bicycle power meter module of claim 1 wherein said first and second stretch sensors are arranged with each said first layer in facing relation.

5. The bicycle power meter module of claim 1 wherein said first and second stretch sensors are arranged with each said second layer in facing relation.

6. The bicycle power meter module of claim 1 wherein said signal processing unit further includes a bridge circuit having said first and second stretch sensors connected in a first branch and a pair of fixed resistances connected in a second branch; an amplifier coupled to said bridge circuit for amplifying signals representative of said total resistance value; an analog-to-digital converter coupled to said amplifier for converting the signals output from said amplifier to digital signals; and a microcomputer coupled to said analog-to-digital converter for receiving said digital signals and said bicycle velocity signals from said associated bicycle speedometer and converting the received signals to said power signals.

7. The bicycle power meter module of claim 6 further including a transmitter coupled to said microcomputer for receiving said power signals and generating equivalent wireless signals; and an antenna coupled to said transmitter for broadcasting said equivalent wireless signals to an associated receiver.

8. A bicycle comprising:
a frame with a rear portion and a rear axle with an externally threaded end portion adjacent said rear portion of said frame; and
a bicycle power meter module comprising an elongate base member having a first end with an aperture, a second end secured to said rear portion of said frame, and a compressible central portion; a strain gauge sensor assembly mounted on said compressible central portion, said strain gauge sensor assembly having first and second stretch sensors each including a first layer having a variable resistance element mounted thereon and a second layer for supporting said first layer, the variable resistance elements of said first and second stretch sensors being ohmically interconnected to present a total resistance value representative of cyclist force; a mounting nut firmly secured to said first end of said base member, said nut having a centrally located internally threaded through-hole in registration with said aperture, said nut being threaded onto said externally threaded axle end portion so that said base member is secured to said axle end portion at said first end of said base member; and a signal processing unit mounted on said base member and electrically coupled to said strain gauge sensor assembly for converting said total resistance value and bicycle velocity signals from an associated bicycle speedometer to cyclist power signals.

9. The bicycle of claim 8 wherein said compressible central portion of said base member has a width less that the width of said first and second ends to promote compression of said central portion under applied force.

10. The bicycle of claim 8 further including a mounting clamp secured to said second end of said base member, said mounting clamp having a mounting band firmly secured to said rear portion of said frame.

11. The bicycle of claim 8 wherein said first and second stretch sensors are arranged with each said first layer in facing relation.

12. The bicycle of claim 8 wherein said first and second stretch sensors are arranged with each said second layer in facing relation.

13. The bicycle of claim 8 wherein said signal processing unit further includes a bridge circuit having said first and second stretch sensors connected in a first branch and a pair of fixed resistances connected in a second branch; an amplifier coupled to said bridge circuit for amplifying signals representative of said total resistance value; an analog-to-digital converter coupled to said amplifier for converting the signals output from said amplifier to digital signals; and a microcomputer coupled to said analog-to-digital converter for receiving said digital signals and said bicycle velocity signals from said associated bicycle speedometer and converting the received signals to said power signals.

14. The bicycle of claim 13 further including a transmitter coupled to said microcomputer for receiving said power signals and generating equivalent wireless signals; and an antenna coupled to said transmitter for broadcasting said equivalent wireless signals to an associated receiver.

* * * * *